Figure 1:
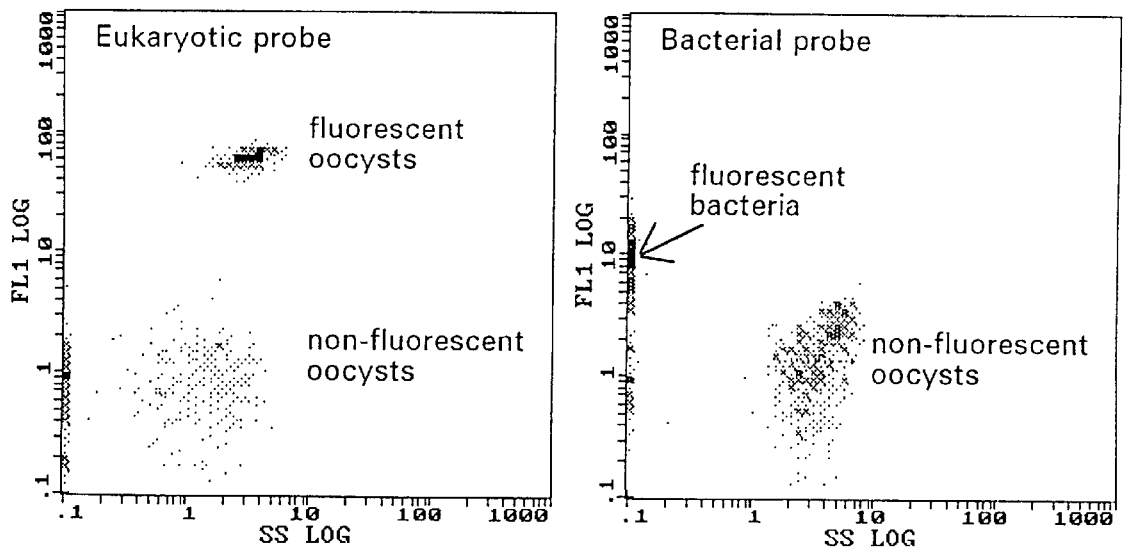

United States Patent [19]
Williams et al.

[11] Patent Number: 6,146,855
[45] Date of Patent: Nov. 14, 2000

[54] **METHOD FOR THE DETECTION OF VIABLE *CRYPTOSPORIDIUM PARVUM* OOCYSTS**

[75] Inventors: Keith Leslie Williams, Frenchs Forest; Graham Vesey, Drummoyne; Duncan Veal, Turramurra; Nicholas John Ashbolt, Potts Point; Matthias Dorsch, Lane Cove, all of Australia

[73] Assignees: Macquarie Research, Ltd.; Australian Water Technologies Pty. Ltd., both of Sydney, Australia

[21] Appl. No.: 08/952,376

[22] PCT Filed: May 6, 1996

[86] PCT No.: PCT/AU96/00274

§ 371 Date: Mar. 3, 1998

§ 102(e) Date: Mar. 3, 1998

[87] PCT Pub. No.: WO96/34978

PCT Pub. Date: Nov. 7, 1996

[30] Foreign Application Priority Data

May 5, 1995 [AU] Australia ................. PN2831

[51] Int. Cl.[7] ............. C12Q 1/68; C07H 21/04; C12P 19/34
[52] U.S. Cl. ............. 435/91.2; 435/6; 536/23.1; 536/24.3
[58] Field of Search ............. 536/24.33, 24.31, 536/24.3; 435/252.1, 91.1, 91.2, 6

[56] References Cited

PUBLICATIONS

Kilani, R. and W. Wenman, "Geographical Variation in 18S rRNA gene sequence of *Cryptospridium Parvum*", International Journal for Parasitology, 303–306, 1994.

Cai, J et al., "PCR cloning and nucleotide sequence determination of the 18S rRNA genes and ITS1 of protozoan parasites *Cryptosporidium parvum* and *Cryptosporidium muris*", Biochim. Biophys. Acta, 317–320, 1992.

Vessey et al, "The use of a rRNA targeted oligonucleotide probe for fluorescent labelling of vialbe *C. parvum* oocysts", J. of Applied Microbiology, 429–440, 1998.

Champliaud et al. "Failure to Differentiate *C. parvum* from *C. meleagridi* based on PCR amplification of eight DNA sequences" Applied Environmental Microbiology, 1454–1458, Apr. 1998.

Morgan et al. "Differntiation between Human and Animal isolates of *C. parvum* using rDNA sequencing and direct PCR analysis", J. Parasitology, 825–830, 1997.

*Primary Examiner*—Lisa B. Arthur
*Assistant Examiner*—Jeanine Enewold
*Attorney, Agent, or Firm*—Barnes & Thornburg; Alice O. Martin

[57] ABSTRACT

Oligonucleotide molecules and methods are disclosed for the detection of viable oocysts or other cells of the protozoa species, *Cyrptosporidium parvum*. Preferred oligonucleotide molecules are selected from the group comprising oligonucleotides having one or more of the following sequences: (a) ACA ATT ATT, (b) CTT TTT GGT, (c) ATT TTA TAT AAA ATA TTT TGA TGA A, (d) TTT TTT TTT TTA GTA T, (e) TAT ATT TTT TAT CTG, (f) CTT TAC TTA CAT GGA TAA CCG, or comprising a part of the sequences (a) to (f) above so as to allow specific hybridization to unique 18S rRNA sequences of *C. parvum*.

11 Claims, 4 Drawing Sheets

Fig. 3A

Sequence 1: C. parvum, 18S complete, 1750bp, L16997
Sequence 2: C. muris, 18S complete, 1743bp, L19069
Sequence 3: C. baileyi, 18S complete, 1733bp, L19068
Sequence a: C. parvum, Macquarie Uni, 18S, primer 180R

```
1 AACCTGGTTGATCCTGCCAGTAGTCATATGCTTGTCTCAAAGATTAAGCCATGCATGTCT
2 AACCTGGTTGATCCTGCCAGTAGTCATATGCTTGTCTCAAAGATTAAGCCATGCATGTCT
3 AACCTGGTTGATCCTGCCAGTAGTCATATGCTTGTCTCAAAGATTAAGCCATGCATGTCT

1 AAGTATAAACTTTTATACGGTTAAACTGCGAATGGCTCATTATAACAGTTATAGTTTACT
a              ATACGGTTAAACTGCGAATGGCTCATTATAACAGTTATAGTTTACT
2 AAGTATAAGCTTTTATACGGCGAAACTGCGAATGGCTCATTAAAACAGTTATAGTTTACT
3 AAGTATAAGCTTCTATACGGCTAAACTGCGAATGGCTCATTATAACAGTTATAGTTTACT
                  'f'
1 TGATAATCTTTTACTTACATGATAACCGTGGTAATTCTAGAGCTAATACATGCGAAAAA
a TGATAATCTTT-ACTTACATGATAACCGTGGTAATTCTA End seq.
2 TGATAATCAAAA--CTGCATGGATAACCGTGGTAATTCTAGAGCTAATACATGCGAAAAA
3 TGATAATCCTTA--CTACATGGATAACCGTGGTAATTCTAGAGCTAATACATGCGAAAAG 1 ACTCGACTTTATGGAAGGGTTGTATTTATTAGATAAAGAACCAATATAATTGGTGACTCA
2 ACCCAACTTCGCGGAAGGGTTGTATTTATTAGATAAAGAACCAATGAGCTTGGTGATTCA
3 ACCCGACTTCTCGGAAGGGTTGTATTTATTAGATAAAGAACCAATACTCTTGGTGACTCA
                       'g'
1 TAATAACTTTACGGATCACAATTA--ATGTGACATATCATTCAAGTTTCTGACCTATCAGCT
2 TAATAACTTTACGGATCGCATCTCTGATGCGACATATCATTCAAGTTTCTGACCTATCAGCT
3 TAATAACTTTACGGATCACATTT---ATGTGACATATCATTCAAGTTTCTGACCTATCAGCT 1 TTAGACGGTAGGGTATTGGCCTACCGTGGCAATGACGGGTAACGGGGAATTAGGGTTCGA
2 TTAGACGGTAGGGTATTGGCCTACCGTGGCTATGACGGGTAACGGGGAATTAGGGTTCGA
3 TTAGACGGTAGGGTATTGGCCTACCGTGGCTATGACGGGTAACGGGGAATTAGGGTTCGA 1 TTCCGGAGAGGGAGCCTGAGAAACGGCTACCACATCTAAGGAAGGCAGCAGGCGCGCAAA
2 TTCCGGAGAGGGAGCCTGAGAAACGGCTACCACATCTAAGGAAGGCAGCAGGCGCGCAAA
3 TTCCGGAGAGGGAGCCTGAGAAACGGCTACCACATCTAAGGAAGGCAGCAGGCGCGCAAA
                                                      'b'
1 TTACCCAATCCTAATACAGGGAGGTAGTGACAAGAAATAACAATACAGGACTTTTTGGTT
2 TTACCCAATCCTGACACAGGGAGGTAGTGACAAGAAATAACAATACAGGGCCTAACGGTC
3 TTACCCAATCCTGACACAGGGAGGTAGTGACAAGAAATAACAATACAGGGCCTAACGGTC 1 TTGTAATTGGAATGAGTTAAGTATAAACCCCTTTACAAGTATCAATTGGAGGGCAAGTCT
2 TTGTAATTGGAATGAGTGAAGTATAAACCCCTTTACGAGTATCAATTGGAGGGCAAGTCT
3 TTGTAATTGGAATGAGTTAAGTATAAACCCCTTTACAAGTAGCAATTGGAGGGCAAGTCT
```

Fig. 3B

```
1 GGTGCCAGCAGCCGCGGTAATTCCAGCTCCAATAGCGTATATTAAAGTTGTTGCAGTTAA
2 GGTGCCAGCAGCCGCGGTAATTCCAGCTCCAATAGCGTATATTAAAGTTGTTGCAGTTAA
3 GGTGCCAGCAGCCGCGGTAATTCCAGCTCCAATAGCGTATATTAAAGTTGTTGCAGTTAA
                                     'c'
1 AAAGCTCGTAGTTGGATTTCTGTTAAT AATTTATATAAAATATTTTGATGAA TATTTATA
2 AAAGCTCGTAGTTGGATTTCTGTTGTATAATTTATAATATTACCAAGGTAATTATTATAT
3 AAAGCTCGTAGTTGGATTTCTGTTAAT       ACTTATATACAATACCACGGTATTTATA
                           'd'
1 TAATATTAACATAATTCATATTACTA TTTTTTTTTTTAGTAT ATGAAATTTTACTTTGAG
2 TATC    AACATCCTTCCTATTA TATTCTAAA       TATATAGGAAATTTTACTTTGAG
3 TAACATTAACATAATTCACATTACTTATTTAAA        GTATGTGAAACTTTACTTTGAG

1 AAAATTAGAGTGCTTAAAGCAGGCATATGCCTTGAATACTCCAGCATGGAATAATATTAA
2 AAAATTAGAGTGCTTAAAGCAGGCAACTGCCTTGAATACTCCAGCATGGAATAATAAGTA
3 AAAATTAGAGTGCTTAAAGCAGGCTATTGCCTTGAATACTCCAGCATGGAATAATATTAA

1 AG ATTTTATCTTTTTTATTGGTTCTAAGATAAGAATAATGATTAATAGGGACAGTTGGG
2 AGGACTTTTGTCTTTCTTATTGGTTCTAGGACAAAAGTAATGGTTAATAGGGACAGTTGGG
3 AG ATTTTATCTTTCTTATTGGTTCTAGGATAAAAATAATGATTAATAGGGACAGTTGGG

1 GGCATTTGTATTTAACAGTCAGAGGTGAAATTCTTAGATTTGTTAAAGACAAACTAATGC
2 GGCATTCGTATTTAACAGCCAGAGGTGAAATTCTTAGATTTGTTAAAGACGAACTACTGC
3 GGCATTTGTATTTAACAGTCAGAGGTGAAATTCTTAGATTTGTTAAAGACAAACTACTGC

1 GAAAGCATTTGCCAAGGATGTTTTCATTAATCAAGAACGAAAGTTAGGGGATCGAAGACG
2 GAAAGCATTTGCCAAGGATGTTTTCATTAATCAAGAACGAAAGTTAGGGGATCGAAGACG
3 GAAAGCATTTGCCAAGGATGTTTTCATTAATCAAGAACGAAAGTTAGGGGATCGAAGACG

1 ATCAGATACCGTCGTAGTCTTAACCATAAACTATGCCAACTAGAGATTGGAGGTTGTTCC
2 ATCAGATACCGTCGTAGTCTTAACCATAAACTATGCCGACTAGAGATTGGAGGTTGTTCC
3 ATCAGATACCGTCGTAGTCTTAACCATAAACTATGCCGACTAGAGATTGGAGGTTGTTCC

1 TTACTCCTTCAGCACCTTATGAGAAATCAAAGTCTTTGGGTTCTGGGGGAGTATGGTCG
2 TTACTCCTTCAGCACCTTATGAGAAATCAAAGTTTTTGGGTTCTGGGGGAGTATGGTCG
3 TTACTCCTTCAGCACCTTATGAGAAATCAAAGTCTTTGGGTTCTGGGGGAGTATGGTCG

1 CAAGGCTGAAACTTAAAGGAATTGACGGAAGGGCACCACCAGGAGTGGAGCCTGCGGCTT
2 CAAGGCTGAAACTTAAAGGAATTGACGGAAGGGCACCACCAGGAGTGGAGCCTGCGGCTT
3 CAAGGCTGAAACTTAAAGGAATTGACGGAAGGGCACCACCAGGAGTGGAGCCTGCGGCTT

1 AATTTGACTCAACACGGGAAAACTCACCAGGTCCAGACATAGGAAGGATTGACAGATTGA
2 AATTTGACTCAACACGGGAAAACTCACCAGGTCCAGACATAGGAAGGATTGACAGATTGA
3 AATTTGACTCAACACGGGAAAACTCACCAGGTCCAGACATAGGAAGGATTGACAGATTGA

1 TAGCTCTTTCTTGATTCTATGGGTGGTGGTGCATGGCCGTTCTTAGTTGGTGGAGTGATT
```

Fig. 3c

```
2 TAGCTCTTTCTTGATTCTATGGGTGGTGGTGCATGGCCGTTCTTAGTTGGTGGAGTGATT
3 TAGCTCTTTCTTGATTCTATGGGTGGTGGTGCATGGCCGTTCTTAGTTGGTGGAGTGATT

1 TGTCTGGTTAATTCCGTTAACGAACGAGACCTTAACCTGCTAAATAGACATAAGAAATAT
2 TGTCTGGTTAATTCCGTTAACGAACGAGACCTTAACCTGCTAAATACGTAATAGAAATTT
3 TGTCTGGTTAATTCCGTTAACGAACGAGACCTTAACCTGCTAAATAGACATAAGAAAATT
           'e'
1 TATATTTTTTATCTG TCTTCTTAGAGGGACTTTGTATGTTTAATACAGGGAAGTTTTAGG
2 TATTTCTATCTTA--TCTTCTTAGAGGGACTTTGCGTGCCTAACGCGAGGAAGTTTGAGG
3 ATTTC    TTATCTGTCTTCTTAGAGGGACTTTGTGTGTTTAACACGAGGAAGTTTTAGG

1 CAATAACAGGTCTGTGATGCCCTTAGATGTCCTGGGCCGCGCGCGCGCTACACTGATGCA
2 CAATAACAGGTCTGTGATGCCCTTAGATGTCCTGGGCCGCACGCGCGCTACACTGATGCA
3 CAATAACAGGTCTGTGATGCCCTTAGATGTCCTGGGCCGCGCGCGCGCTACACTGATGCA

1 TCCATCAAGTATATATTCCTGTTTCGAAGGAAATGGGTAATCTTTTGAATATGCATCGTG
2 TCCAGCGAGTATATAT-CCTGTTTCGAAGGAAATGGGTAATCTTATGAGTATGCATCGTG
3 TCCATCAAGTAT TCT CCTGTTTCGAAGGAAATGCGTAATCTTATGAATATACATCGTG

1 ATGGGGATAGATCATTGCAATTATTGATCTTGAACGAGGAATTCCTAGTAAGCGCAAGTC
2 ATGGGGATAGATCATTGCAATTATTGATCTTTAACGAGGAATTCCTAGTAAGCGCAAGTC
3 ATGGGGATAGATCATTGCAATTATTGATCTTCAACGAGGAATTCCTAGTAAGCGCAAGTC

1 ATCAGCTTGCGCTGATTACGTCCCTGCCCTTTGTACACACCGCCCGTCGCTCCTACCGAT
2 ATCAGCTTGCGCTGATTACGTCCCTGCCCTTTGTACACACCGCCCGTCGCTCCTACCGAT
3 ATCAGCTTGCGCTGATTACGTCCCTGCCCTTTGTACACACCGCCCGTCGCTCCTACCGAT

1 TGAATGATCCGGTGAATTATTCGGACCATACTTT-GTAGCAAT-ACAT-GTAAGGAAAGTTTC
2 TGAGTGATCCGGTGAATAATTCGGACCATGCTACAGTAGCAATTACATAGCAAGGGAAGTTTC
3 TGAGTGATCCGGTGAATTATTCGGACCATACATAAGTAGCAAT ACAT GTAAGGAAAGTTTT

1 GTAAACCTTATCATTTAGAGGAAGGAGAAGTCGTAACAAGGTTTCCGTAGGTGAACCTGC
2 GTAAACCTTATCACTTAGAGGAAGGAGAAGTCGTAACAAGGTTTCCGTAGGTGAACCTGC
3 GTAAACCTTATCACTTAGAGGAAGGAGAAGTCGTAACAAGGTTTCCGTAGGTGAACCTGC

1 AGAAGGATCA
2 AGAAGGA
3 AGAAGGATCA
```

METHOD FOR THE DETECTION OF VIABLE *CRYPTOSPORIDIUM PARVUM* OOCYSTS

FIELD OF THE INVENTION

The present invention relates to a method for the detection of viable oocysts or other cells of the protozoa species *Cryptosporodium parvum*. More particularly the invention relates to a method for such detection utilising one or more of a number of probes capable of hybridising to specific *C. parvum* 18S rRNA sequences.

BACKGROUND ART

The detection of Cryptosporidium oocysts in water presently relies on the concentration of particulate matter from large volumes of water prior to staining with fluorescently labelled monoclonal antibodies. Until recently, detection and identification of fluorescently labelled oocysts required examination of the sample using epifluorescence microscopy. The tedious and labour intensive nature of this detection method,. in particular the amount of fluorescent microscopy required, limited the monitoring work which could be performed. The development of flow cytometric assisted detection methods has alleviated some of these problems and enabled the routine monitoring of water for the presence of Cryptosporidium oocysts (Vesey et al., 1994A). However, a major limitation of all these methodologies is the lack of oocyst viability measurements. Methods to determine viability such as animal infectivity and excystation, are impractical because of the low number of oocysts normally present in water samples and the tedious nature of such tests.

The presence of dead Cryptosporidium oocysts in drinking water is of little significance to public health, however if oocysts are viable the risk to public health is enormous. Moreover, of the seven species of Cryptosporidium; *C. parvum, C. muris, C. meleagridis, C. serpentis, C. nasorum, C. wrairi* and *C. baileyi* only one, *C. parvum* is infectious to humans (Rose et al., 1988), and yet all the currently available monoclonal antibodies are not species specific. There is therefore, an urgent requirement to develop an effective method for determining the viability of *C. parvum* oocysts in water.

Fluorescence in situ hybridisation (FISH) is a relatively new method by which microorganisms can be specifically labelled. The technique is reliant upon the identification of a specific sequence of nucleic acid within the target organism. Probes targeting a specific nucleic acid sequence are then synthesised and labelled with a fluorochrome. The cell is then permeabilised and the complementary sequence allowed to hybridise with the target sequence resulting in specific labelling of the target cell.

The use of ribosomal RNA (rRNA) targeted oligonucleotide probes with FISH and flow cytometry has been reported by Amann et al. (1990B). Molecules of rRNA are ideal targets for fluorescently labelled nucleic probes for several reasons: (1) high sensitivity can be achieved since the target molecules are present in very high numbers; (2) a denaturation step is not required during the procedure as the target region is single stranded; and (3) rRNA has a short half life and will only be present in a high copy number in viable cells.

DISCLOSURE OF THE INVENTION

In a first aspect, the present invention provides an oligonucleotide molecule for the detection of viable cells of

*Cryptosporidium parvum* (*C. parvum*), the oligonucleotide molecule characterised in that it specifically hybridises to unique 18S rRNA sequences of *C. parvum.*

Preferably, the oligonucleotide molecule specifically hybridises to unique 18S rRNA sequences of *C. parvum* under medium to high stringency conditions (Sambrook et al., 1989.), however, in most cases, conditions of high stringency will be required to ensure specific hybridisation to unique *C. parvum* 18S rRNA sequences.

In a preferred embodiment of the invention, the oligonucleotide molecule is selected from the group comprising oligonucleotides that hyloridize with one or more of the following nucleotide sequences:

(a) AAT TTA TAT AAA ATA TTT TGA TGA A (SEQ ID NO: 1)

(b) TTT TTT TTT TTA GTA T (SEQ ID NO: 2)

(c) TAT ATT TTT TAT CTG (SEQ ID NO: 3)

(d) CTT TAC TTA CAT GGA TAA CCG (SEQ ID NO: 4)

or comprising a part of the sequences (a) to (d) above or comprising a part of the sequences (a) to (f) above so as to allow specific hybridisation to unique 18S rRNA sequences of *C. parvum.*

Preferably, the oligonucleotide molecules according to the invention are detectably labelled so that they may be utilised as probes in hybridisation assays. However, oligonucleotide molecules which are not labelled may be used in a polymerase chain reaction (PCR) to amplify a part of the rRNA of *C. parvum* to allow its detection.

In a second aspect, the present invention consists in a method for the detection of the presence of viable cells of *C. parvum* in a sample, comprising the steps of adding to the sample a probe consisting of a detectably labelled oligonucleotide molecule according to the first aspect of the invention; permeabilising or lysing the cells present in the sample to allow hybridisation of the probe to the 18S rRNA of any *C. parvum* cells present in the sample; and detecting the hybridisation of the probe to cells in the sample.

In a preferred embodiment, the second aspect of the invention is used in combination with fluorescence in situ hybridisation (FISH) in which the oligonucleotide probe is labelled with fluorochrome and the resulting fluorescent cell is detected by flow cytometry.

In a further preferred embodiment of the invention, several different oligonucleotide probes are used and are distinguished by the use of different labels. More preferably the oligonucleotide probes are labelled with different fluorochromes and detected by flow cytometry.

While it is preferred that the probes are fluorescently labelled it is to be understood that other known forms of labelling may be used within the broad scope of the present invention. Examples of other forms of labelling are radioactivity and chemiluminescence.

The oligonucleotide molecules and methods of the invention, may be used to detect the presence in a sample of any type of viable cell of *C. parvum*. Normally only oocysts will be found in environmental samples. Other cell types may, however, be found and detected in clinical samples.

BRIEF DESCRIPTION OF THE DRAWINGS

FIG. 1 shows the results of flow cytometric analysis of FISH stained oocysts using a eukaryotic specific probe (Euk probe) and a bacterial specific probe (Bac probe).

FIG. 2 shows the comparison of oocyst viability as measured by excystation and viability determined by FISH on oocysts following storage at 22° C. in the dark and sampled over a 74 day period.

FIG. 3 shows the position of the specific C. parvum 18S rRNA probes in respect of the whole 18S rRNA sequence. The various sequences shown are:

Sequence 1: C. parvum, 18S complete, 1750 bp, L16997.

Sequence 2: C. muris, 18S complete, 1743 bp, L19069.

Sequence 3: C. baileyi, 18S complete, 1733 bp, L19068.

Sequence 4: C. parvum, Macquarie Uni, 18S, primer 180R.

BEST MODE OF CARRYING OUT THE INVENTION

MATERIALS AND METHODS

Cryptosporidia

*Cryptosporidium parvum*. *Cryptosporidium parvum* oocysts cultured in lambs and purified by density gradient centrifugation were purchased from the Moredun Animal Research Institute, Edinburgh. UK.

Eukaryotic Specific and Eubacterial Specific Probes

Oligodeoxynucleotide probes. A probe (Euk) complementary to a 18S rRNA region conserved for Eucarya (5'-ACCAGACTTGCCCTCC-3') (Amann et al., 1990) was used to stain Cryptosporiduium oocysts. A second probe (Bac) complementary to a 16S rRNA region conserved for all bacteria (5'-GCTGCCTCCCGTAGGAGT-3') (Amann et al., 1990) was used as a negative control for non-specific binding in all experiments. The probes were synthesised and labelled with fluorochromes as described previously (Wallner et al., 1993).

Design of a Specific FISH-Probe for C. parvum

Extraction of genomic DNA: Oocysts were pelleted by centrifugation, resuspended in TE buffer, and repeatedly frozen in a mixture of dry ice and ethanol and thawed by boiling for 2 mins. After incubation with SDS and proteinase K (1% w/v 100 µg/ml respectively)for 1 h at 37° C. the lysate was extracted with phenol, phenol-chloroform and chloroform-isoamylalcohol. Nucleic acid was precipitated with 1 volume 4M ammonium acetate pH 4.5 and 2 volumes isopropanol, washed with 70% ethanol, dried, and finally dissolved in distilled water.

Sequence analysis and probe/primer design. Complete 18S rRNA sequences comprising the species *C. parvum, C. muris* and *C.baileyi* were obtained through the EMBL and GenBank data bases. The sequences were manually aligned. One particular region appeared to have the potential to discriminate C. parvum from the other species included in the analysis. To examine the validity of the published 18S rRNA sequence of C. parvum a short stretch of C. parvum rDNA including one of the putative probe regions (Table 1, Letter f) was sequenced. Two primers targeting the conserved 5'- and 3'- end of the 18S rDNA were designed (5'AAC CTG GTT GAT CCT GCC FORWARD and 3'GGT TCA CCT ACG GAA ACC REVERSE) and employed to amplify the gene via PCR as described previously for 16S rDNA (Dorsch and Stackebrandt, 1992). The probe region was then sequenced using a reverse primer (CCT TCC ATA AAG TCG AGT) complementary to a sequence approximately 50 nucleotides downstream. The sequencing protocol was as described (Dorsch and Stackebrandt, 1992). Our results clarified the ambiguity in the literature concerning the published C. parvum 18S rRNA sequence (see FIG. 3). The accessibility of the target region within native ribosomes for fluorescence in situ hybridisation was estimated using a secondary structure model for the 18S rRNA of angiosperms (Schmidt-Puchta et al., 1989), and six sequences were identified as being specific to C. parvum (Table 1).

TABLE 1. Sequences for preparing specific probes for target sites of 18S ribosome for *Cryptosporidium parvum*. The position of the target sites with respect to the whole 18S rRNA sequence are shown in FIG. 3.

| Letter | Sequence |
| --- | --- |
| a | ACA ATT AAT |
| b | CTT TTT GGT |
| c | AAT TTA TAT AAA ATA TTT TGA TGA A |
| d | TTT TTT TTT TTA GTA T |
| e | TAT ATT TTT CTG |
| f(CRY1) | CTT TAC TTA CAT GGA TAA CCG |

A fluorescently labelled probe was designed for sequence number 6 (CGG TTA TCC ATG TAA GTA AAG).

Oligonucleotide synthesis. Oligonucleotides of the *C. parvum* specific probe number 6 (CRY1) were synthesised and labelled with FITC by Biotech Int. (Perth).

SAMPLE PREPARATION

Fixation of oocysts. Fixation of oocysts was performed using a modified method of that described previously by Wallner et al. (1993) for the fixation of yeasts and bacteria. One volume of oocyst suspension containing approximately $10^7$ oocysts, was mixed with three volumes of fresh cold 4% w/v paraformaldehyde in phosphate buffered saline (PBS), pH 7.2, and kept at 4° C. for 1 h. The oocysts were washed three times by centrifugation (13.000 g. 30 s) and then resuspended in PBS. The sample was then mixed with an equal volume of cold (−20° C.) absolute ethanol and hybridised within 1 h or stored at 4° C.

Hybridisation. Fixed oocysts were hybridised with the probe by mixing 10 µl of oocyst suspension with 100 µl of hybridisation buffer (0.9 M NaCl, 20 mM Tris/HCl pH 7.2, 0.5% w/v sodium dodecylsulfate) prewarmed to 48° C. and then 10 µl of probe added (25 ng/µl in distilled water). The sample was mixed and incubated at 48° C. for 1 h. The sample was then washed by centrifugation (13,000 g, 30 s) and resuspended in hybridisation buffer, without sodium dodecylsulfate, prewarmed to 48° C. Samples were then analysed immediately using flow cytometry or epifluorescence microscopy.

Sample analysis. Flow cytometry was performed using a Coulter Elite flow cytometer or a Coulter XL flow cytometer as described previously (Vesey et al., 1993; Vesey et al., 1994A; Vesey et al., 1994B).

Epifluorescence microscopy was performed using a Nikon Optiphot-2 microscope fitted with differential interference contrast (DIC) optics and excitation and emission filters suitable for the examination FITC. Oocysts were detected using DIC and then examined for fluorescence. A minimum of 100 oocysts were examined in each sample.

Excystation. In vitro excystation was performed as described by Campbell et al. (1992). To a 100 µl volume of oocyst suspension (approximately $10^4$ oocysts), 10 µl of 1 (w/v) sodium deoxycholate in Hanks minimal essential medium and 10 µl of 2.2% sodium hydrogen carbonate in Hanks balanced salt solution are added. After incubation, 37° C. for 4 h, samples were examined microscopically using DIC optics. The proportion of empty oocysts, partially excysted oocysts and non-excysted oocysts were determined. At least 100 oocysts were counted in each sample. The percent excystation was calculated as follows:

(number of empty oocysts+number of partially excysted oocysts)/×100 total number of oocysts counted where the number of empty oocysts equalled the number pre-excystation subtracted from the number post excystation.

Stored samples. To determine if samples could be fixed and then stored before analysis, storage experiments were performed. Aliquots (100µl) of fixed oocyst suspensions were stored at 4° C. for 1 month. Samples were removed at time intervals, stained with FISH using the eukaryotic specific probe and analysed using flow cytometry. All experiments were performed in triplicate.

Aging of oocysts. Aliquots (10 µl) of oocyst suspensions containing $10^8$ oocysts were diluted in 10 ml of PBS and stored at 22° C. in the dark. Samples (0.5 ml) were taken at time intervals and the viability of oocysts assessed using both FISH with the eukaryotic specific probe and excystation. All experiments were performed in triplicate.

RESULTS

Staining of oocysts with FISH. Microscopic examination of oocysts, which had been stained using fluorescence in situ hybridisation with the Euk rRNA probe, revealed brightly fluorescent oocysts together with oocysts which showed no fluorescence. Fluorescent staining was located within the sporozoites. Examination of the fluorescent oocysts using DIC optics revealed intact oocysts with a small gap between the oocyst wall and the internal structures. In comparison, non-fluorescent oocysts frequently appeared to have a ruptured oocyst wall and a large gap between the oocyst wall and the internal structures. Empty oocysts did not fluoresce.

Flow cytometric analysis of oocysts stained by FISH with the Euk rRNA probe resulted in two distinct populations, a brightly fluorescent population and a non-fluorescent population indicating viable and non-viable populations respectively. This is illustrated in the scatter plot (FIG. 1) in which the Y axis represents fluorescence and the X-axis side scatter. Analysis by epifluorescence microscopy and flow cytometry of samples which had been stained with the Bac probe resulted-in no fluorescence in any oocysts above that of the autofluorescence of unstained oocysts (FIG. 1).

Stored samples. Samples of fixed oocysts which had been stored at 4° C. for up to 4 weeks and then stained with FISH using the Euk probe showed no reduction in the number of oocysts which fluoresced and no reduction in the brightness of fluorescence (Table 2).
TABLE 2. A comparison of the fluorescence intensity of freshly fixed oocysts and oocysts fixed and stored at 4° C. for up to 3 weeks, before staining with FISH and analysed using flow cytometry.

| Day | Mean Fluorescence |
|---|---|
| 0 | 17.1 |
| 7 | 17.3 |
| 14 | 16.6 |
| 21 | 17.8 |

Comparison of viability determined by FISH and in vitro excystation. A comparison of oocyst viability, measured by excystation and staining by FISH with the Euk and CRY1 probes on batches of oocysts obtained from Moredun Animal Research Institute are presented in Table 3. Results were very similar for both methods of assessing oocyst viability indicating that the rRNA probes only stain viable oocysts.
TABLE 3. Comparison of oocyst percentage viability determined by excystation and viability determined by FISH on three different batches of oocysts.[1]

| | Batch 1 (Euk) | Batch 2 (Euk) | Hatch 3 (Euk) | Batch 4 (CRY1) |
|---|---|---|---|---|
| FISH | 56% (1.2)[2] | 76% (3.7) | 95% (2 2) | 71% |
| Excystation | 54% (2 7) | 79% (2.8) | 92% (4 9) | 69% |

[1]100 oocysts were examined for each determination.
[2]Standard Deviation.

[1]100 oocysts were examined for each determination.
[2]Standard Deviation.

Figure 2:
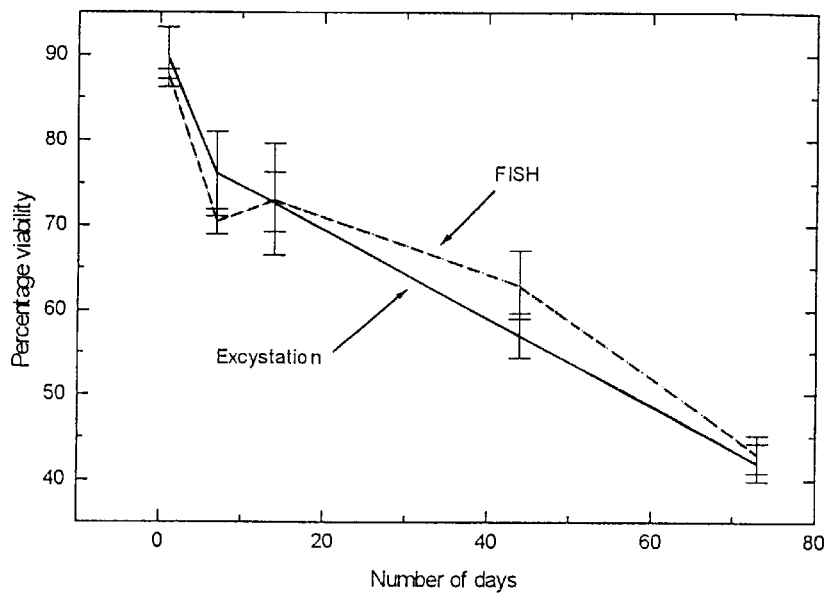

Comparison of FISH and excystation for determining oocyst viability on suspensions of oocysts stored at 22° C. in the dark are presented in FIG. 2. Results are very similar for both methods. A gradual decline in the viability of the oocysts from 90% to 40% over the 74 day period was observed with both methods. Correlation of the two sets of results was highly significant, with a calculated correlation coefficient (r) of 0.998.

The present inventors have developed a method using FISH and a rRNA directed probe to assess the viability of Cryptosporidium sp. oocysts. However, the invention is not restricted to oocysts. The unique 18S rRNA sequence of *C. parvum* identified and the method of the detection as stated, may also be used to detect other life stages of the *C. parvum* organism.

The preferred method for detecting the unique 18S rRNA sequences of *C. parvum* in an environmental sample is the use of labelled oligonucleotide probes.

Oocysts containing fluorescing sporozoites after hybridisation with the probes are viable and oocysts which do not fluoresce are dead. The reason that dead oocysts do not stain is because the rRNA which the probes bind to deteriorates rapidly and in dead oocysts is not present in sufficient copy numbers to be detected.

It is envisaged that the PCR may be used to detect viable *C. parvum* cells. In a PCR reaction, one of the specific oligonucleotide molecules, as disclosed, may be used in combination with a second oligonucleotide molecule (which may or may not be specific to *C. parvum*) to amplify 18S rRNA sequences from *C. parvum*. The amplified sequence will contain at least part of one of the unique sequences of *C. parvum*. The oligonucleotides in the PCR reaction may also be labelled. The employment of PCR to detect viable *C. parvum* would be useful in analysis of body fluids or excretions from animals, including humans.

In vitro excystation is currently considered the gold standard to which methods for determining oocyst viability are compared. Results from comparing measurement of oocyst viability using FISH and measuring viability using in vitro excystation produced very similar results with both methods for all samples of oocysts analysed. Correlation of the FISH assay with excystation was highly statistically significant with a calculated correlation coefficient of 0.998. Furthermore, the FISH method was found to be easy to perform and the results easily interpreted. Oocysts were either fluorescent, indicating a viable oocyst, or did not fluoresce at all, indicating a dead oocyst.

FISH techniques have the potential to alleviate the problems of assaying environmental water samples through their increased specificity and are ideal staining methods for analysis by flow cytometry.

Another significant advantage of the FISH method is that samples can be fixed and then stored at 4° C. prior to analysis. By contrast. samples which are to be analysed using a known method must be analysed immediately as storage or fixation of the samples will result in a reduction in the viability of the oocysts as measured by this technique.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Amann, R. I., Binder, B. J., Chisholm S. W., Devereux, R., and Stahl, D. (1990A). Combination of 16S rRNA-targeted oligonucleotide probes with flow cytometry for analysing mixed microbial populations, Appl. Environ. Microbiol., 56, 1919–1925.

Amann, R. I., Krumholz, L., and Stahl, D. A. (1990b). Fluorescent-oligonucleotide probing of whole cells for determinative, phlogentic, and environmental studies in microbiology. J. Bacteriol., 172: 762–770.

Campbell, A. T., Robertson, L. J., Smith, H. V. (1992). Viability of *Cryptosporidium parvum* oocysts: correlation of in vitro excystation with inclusion of fluorogenic vital dyes. Appl. Environ. Microbiol., 58: 3488–3493.

Campbell, A. T., Robertson, L. J., Smith, H. V. (1993A). Effects of preservatives on viability of *Cryptosporidium parvum* oocysts. Appl. Environ. Microbiol., 59: 4361–4362.

Campbell, A. T., Robertson, L. J., Smith, H. V. (1993B). Novel methodology for the detection of *Cryptosporidium parvum*: A comparison of cooled charge coupled devices (CCD) and flow cytometry. Wat. Sci. Tech., 27: 89–92.

Robertson, L. J., Campbell, A. T., Smith. H. V. (1992). Survival of *Cryptosporidium parvum* oocysts under various environmental pressures. Appl. Environ. Microbiol., 58: 3494–3500.

Dorsch, M. and Stackebrandt, E. (1992). Some modifications in the procedure of direct sequencing of PCR amplified 16S rDNA. Journal of Microbiological, Sambrook J., Fritsch E. F. and Maniatis T. (1989) In: Molecular Cloning. A Laboratory Manual, Cold Spring Harbor Laboratory Press.

Scmidt-Puchta, W., Kutemeier, G., Gunther, I., Haas, B. and Sanger, H. L. (1989). Secondary structure model for the 18S rRNA of angiosperms. Molecular and General Genetics, 219: 17–25.

Vesey, G., Slade, J. S., Bvrne, M., Shepherd, K., Dennis, P. J. and Fricker, C. R. (1993). Routine monitoring of Cryptosporidium oocysts in water using flow cytometry. J. Appl. Bacteriol., 75: 87–90.

Vesey, G., Hutton, P. E., Champion, A. C., Ashbolt, N. J. Williams, K. L., Warton, A. and Veal, D. A. (1994A). Application of flow cytometric methods for the routine detection of Crytosporidium and Giardia in water. Cytometry, 16: 1–6.

Vesey, G., Narai, J., Ashbolt, N., Williams, K. L. and Veal, D. (1994B). Detection of specific microorganisms in environmental samples using flow cytometry, p.489–522. *In Methods in Cell Biology-Flow Cytometry* Second Edition. Academic Press Inc., New York.

Waliner, G., Amann, R. and Beisker, W. (1993). Optimizing fluorescent in-situ hybridisation with rRNA-targeted oligonucleotide probes for flow cytometric identification of microorganisms. Cytometry, 14: 136–43.

What is claimed is:

1. An oligonucleotide molecule for the detection of viable oocysts of *Cryptosporidium parvum* (*C. parvum*) in an environmental sample to be tested for safety of human use, wherein said molecule specifically hybridizes to a molecule having a DNA sequence of *C. parvum*, said sequence selected from the group consisting of:

(a) AAT TTA TAT AAA ATA TTT TGA TGA A (SEQ ID NO: 1);

(b) TTT TTT TTT TTA GTA T (SEQ ID NO: 2);

(c) TAT ATT TTT TAT CTG (SEQ ID NO: 3);

(d) CTT TAC TTA CAT QGA TAA CCG (SEQ ID NO: 4);

(e) ACA ATT AAT (SEQ ID NO: 5); and (f) CTT TTT GGA (SFQ ID NO: 6);

wherein the molecule allows detection of viable oocysts of *C. parvum*.

2. The oligonucleotide molecule of claim 1, wherein the molecule hybridizes under conditions of moderate or high stringency to rRNA of *C. parvum* oocysts.

3. A composition comprising a plurality of the oligonucleotide molecules of claim 1 wherein a plurality of oligonucleotide molecules with different nucleotide sequences are used, and each molecule is distinguished from other molecules by the use of different detectable labels on each molecule.

4. A method for detection of viable oocysts of *Cryptosporidium parvum* (*C. parvum*) present in an environmental sample to be tested for safety of human use, the method comprising the steps of:

(a) adding to the sample an oligonucleotide molecule of claim 1 which is detectably labeled;

(b) permeabilising or lysing *C. parvum* oocysts present in the sample;

(c) allowing hybridization between the oligonucleotide molecule and the 18S rRNA of the permeabilised or lysed *C. parvum* oocysts; and (d) detecting the hybridization of the molecule to the rRNA in the sample from which detection of the viable oocysts is inferred.

5. The method of claim 4, wherein the environmental sample is water.

6. The method of claim 4, wherein a plurality of oligonucleotide molecules with different nucleotide sequences are used, and each molecule is distinguished from other molecules by the use of different detectable labels on each molecule.

7. The method of claim 4, wherein the oligonucleotide molecule is labeled with a fluorochrome and detection of the hybridization is by flow cytometry.

8. The method of claim 7, wherein the oligonucleotide molecules are each labeled with a different fluorochrome.

9. The method of claim 4, wherein hybridization occurs under conditions of high stringency.

10. A method for tie detection of the presence of viable oocysts of *Cryptosporidium parvum* (*C. parvum*) in an environmental sample, the method comprising:

(a) adding to the sample a first and a second primer, wherein said first primer each consist of an oligonucleotide molecule according to claim 1, and the second primer hybridizes to 18S rRNA of *C. parvum*;

(b) permeabilising or lysing *C. parvum* oocysts present in the sample to allow hybridization of the primer to the 18S rRNA of any *C. parvum* oocysts present in the sample;

(c) conducting a polymerase chain reaction (PCR) to amplify a part of the 18S rRNA or rDNA of *C. parvum*; and (d) detecting the amplified part of the rRNA or rDNA in the sample from which the presence of viable oocysts of *C. parvum* is inferred.

11. The method of claim 10, wherein the environmental sample is water.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AATTTATATA AAATATTTTG ATGAA 25

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear -continued

```
    (ii) MOLECULE TYPE: cDNA (xi) SEQUENCE DESCRIPTION: SEQ ID NO:2:

TTTTTTTTTT TAGTAT                                                      16

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TATATTTTTT ATCTG                                                       15

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CTTTACTTAC ATGGATAACC G                                                21
```